United States Patent [19]
Wang et al.

[11] Patent Number: 6,153,700
[45] Date of Patent: Nov. 28, 2000

[54] WATER-DEGRADABLE FLUSHABLE FILM OF POLYOLEFIN AND POLY(ETHYLENE OXIDE) AND PERSONAL CARE ARTICLE THEREWITH

[75] Inventors: James Hongxue Wang, Appleton, Wis.; David Michael Schertz, Roswell, Ga.

[73] Assignee: Kimberly-Clark Worldwide, Inc., Neenah, Wis.

[21] Appl. No.: 09/094,766

[22] Filed: Jun. 15, 1998

Related U.S. Application Data

[63] Continuation-in-part of application No. 08/813,571, Mar. 6, 1997, abandoned.
[60] Provisional application No. 60/034,616, Dec. 31, 1996.

[51] Int. Cl.[7] ............... A61F 13/15; A61F 13/20; C08L 23/06
[52] U.S. Cl. ............... 525/187; 604/364; 604/370; 604/372
[58] Field of Search ............... 525/187; 604/364

[56] References Cited

U.S. PATENT DOCUMENTS

| | | | |
|---|---|---|---|
| 3,323,978 | 6/1967 | Rasmussen | 161/169 |
| 3,539,666 | 11/1970 | Schirmer | 264/51 |
| 3,717,541 | 2/1973 | Schirmer | 161/169 |
| 3,833,708 | 9/1974 | Miller et al. | 264/344 |
| 3,935,141 | 1/1976 | Potts et al. | 260/23 H |
| 3,954,928 | 5/1976 | Omori et al. | 264/51 |
| 4,018,729 | 4/1977 | Faucher et al. | 260/17 R |
| 4,080,405 | 3/1978 | Agouri et al. | 260/878 R |
| 4,186,233 | 1/1980 | Krajewski et al. | 428/213 |
| 4,415,691 | 11/1983 | Allen et al. | 524/114 |
| 4,590,227 | 5/1986 | Nakamura et al. | 525/54.31 |
| 4,868,222 | 9/1989 | Chau et al. | 521/61 |
| 5,095,619 | 3/1992 | Davis et al. | 30/40 |
| 5,288,532 | 2/1994 | Juhl et al. | 525/187 |
| 5,300,574 | 4/1994 | Bacskai | 525/181 |
| 5,367,003 | 11/1994 | Petcavich | 523/124 |
| 5,369,168 | 11/1994 | Famili et al. | 525/57 |
| 5,391,423 | 2/1995 | Wnuk et al. | 428/217 |
| 5,395,308 | 3/1995 | Fox et al. | 604/15 |
| 5,415,905 | 5/1995 | Middlesworth et al. | 528/35.7 |
| 5,417,679 | 5/1995 | Toms et al. | 604/370 |
| 5,429,874 | 7/1995 | VanPutte | 428/522 |
| 5,446,100 | 8/1995 | Durrance et al. | 525/221 |
| 5,464,687 | 11/1995 | Sheth | 428/286 |
| 5,468,259 | 11/1995 | Sheth et al. | 8/497 |
| 5,489,470 | 2/1996 | Noda | 428/286 |
| 5,498,692 | 3/1996 | Noda | 528/361 |
| 5,498,785 | 3/1996 | Wang et al. | 525/371 |
| 5,509,913 | 4/1996 | Yeo | 604/364 |
| 5,532,066 | 7/1996 | Latiolais et al. | 428/483 |
| 5,540,663 | 7/1996 | Kroner et al. | 428/221 |
| 5,549,791 | 8/1996 | Herron et al. | 162/157.6 |
| 5,641,562 | 6/1997 | Larson et al. | 442/394 |

FOREIGN PATENT DOCUMENTS

| | | |
|---|---|---|
| 52355/93 | 3/1994 | Australia . |
| 0 184 440 | 6/1986 | European Pat. Off. . |
| 0296355 A2 | 12/1988 | European Pat. Off. . |
| 49-126742 | 12/1974 | Japan . |
| 61-272217 | 12/1986 | Japan . |
| 2 295 553 | 6/1996 | United Kingdom . |
| WO 94/00163 | 1/1994 | WIPO . |
| WO 94/00293 | 1/1994 | WIPO . |
| WO 95/11929 | 4/1995 | WIPO . |
| WO 95/20614 | 8/1995 | WIPO . |
| WO 95/20615 | 8/1995 | WIPO . |
| WO 95/20621 | 8/1995 | WIPO . |
| WO 95/23249 | 8/1995 | WIPO . |
| WO 95/23250 | 8/1995 | WIPO . |
| WO 96/21057 | 7/1996 | WIPO . |
| WO 96/21475 | 8/1996 | WIPO . |

OTHER PUBLICATIONS

Bartczak, Z. and A. Galeski, "Changes in Interface Shape Druing Crystallization in Two–Component Polymer Systems", Polymer, 1986, vol. 27, Apr., pp. 544–548.

Mortensen, Kell, "Phase Behavior of Poly(propylene Oxide)–Poly(ethylene oxide)–Poly(propylene oxide) Triblock Copolymer Melt and Aqueous Solutions", Macromolecules, vol. 27, No. 20, 1994, pp. 5654–5666.

Song, Z. and W.E. Baker, "Melt Grafting of T–Butylaminoethyl Methacrylate Onto Polyethylene," Polymer, 1992, vol. 33, No. 15, pp. 3266–3273.

Tang, Tao and Baotong Huang, "Compatibilization of Polypropylene/Poly (Ethylene Oxide) Blends and Crystallization Behavior of the Blends," Journal of Polymer Science: Part B: Polymer Physics, vol. 32, (1994), pp. 1991–1998.

*Primary Examiner*—Robert E. L. Sellers
*Attorney, Agent, or Firm*—Jerry F. Janssen; Thomas D. Wilhelm

[57] ABSTRACT

The invention provides a water-degradable polyolefin-containing film having greater than about 55 weight percent of a polyolefin and less than about 45 weight percent of poly(ethylene oxide) of weight average molecular weight of less than about 100,000. Preferably, the polyolefin is low density polyethylene. The polyolefin-containing film, when immersed in water for about 30 seconds, loses at least 10% in two or more of the tensile properties: percent strain-to-break, peak stress, energy-to-break and modulus when compared to the dry or pre-immersion values.

Also provided are flushable personal care articles such as infant diapers, feminine hygiene napkins, and adult incontinence garments having a backing or barrier layer comprising a water degradable polyolefin-containing film of the invention.

9 Claims, No Drawings

WATER-DEGRADABLE FLUSHABLE FILM OF POLYOLEFIN AND POLY(ETHYLENE OXIDE) AND PERSONAL CARE ARTICLE THEREWITH

CROSS-REFERENCE TO RELATED APPLICATIONS

This application is a continuation-in-part of application Ser. No. 08/813,571 filed Mar. 6, 1997, abandoned which claims priority from Provisional Application Serial No. 60/034,616 filed Dec. 31, 1996, the disclosures of which are incorporated herein by reference.

FIELD OF THE INVENTION

The present invention relates to a water-degradable or flushable polyolefin-containing film. More particularly, the present invention relates to a water-degradable or flushable polyolefin-containing film having greater than about 55 weight percent of a polyolefin and less than about 45 weight percent of poly(ethylene oxide).

BACKGROUND OF THE INVENTION

Personal care products, such as infant diapers, sanitary napkins, adult incontinence garments, and the like are generally constructed from a number of different components and materials. Such articles typically have some portion, usually the backing layer, liner, barrier or baffle constructed of a liquid repellent film material. This repellent material is appropriately constructed to minimize or prevent the exudation of the absorbed liquid from the article and to obtain greater utilization of the absorbent capacity of the product. Liquid repellent films commonly used includes plastic materials such as polyethylene films and the like.

Although such products are relatively inexpensive, sanitary and easy to use, disposal of a soiled product is not without its problems. With greater interest being placed in protecting the environment, there is a need to develop materials that are more compatible with the existing and developing waste disposal technologies while still delivering the performance consumers have come to expect. An ideal disposal alternative would be to use municipal sewage treatment and private residential septic systems. Products suited for disposal in sewage systems can be flushed down a convenient toilet and are termed "flushable."

While flushing such articles would be convenient, the liquid repellent material which normally does not disintegrate in water tends to plug toilets and sewer pipes. It therefore becomes necessary, although undesirable, to separate the barrier film material from the absorbent article prior to flushing.

In addition to the article itself, typically the packaging in which the disposable article is distributed is also made from a water resistant material. Water resistivity is necessary to prevent the degradation of the packaging from environmental conditions and to protect the disposable articles therein. Although this packaging may be safely stored with other refuse for commercial disposal, and especially in the case of individual packaging of the products, it is often more convenient to dispose of the packaging in the toilet with the discarded disposable article. However, in the cases where such packaging is composed of a water resistant material, plugging of the drains to the toilet typically results.

Desirably, a commercial, water degradable or flushable product should be relatively responsive to water and be transportable in a sewer system. Commercially available water-soluble polymers, such as poly(ethylene oxide) (PEO), poly(vinyl alcohol) (PVOH), acrylamide polymers, acrylic acid-based polymers, and cellulose derivatives, possess the desired characteristics for flushability, such as water solubility and/or water dispersibility. However, due to their in-use degradability and storage degradation, these materials function poorly as components in personal care products. Other disadvantages are that these polymers are difficult to process and are substantially more expensive than polyolefins.

The requirements for a functional and flushable product provide a substantial challenge in finding suitable materials with the desired properties. In an attempt to overcome the flushability problem of a water resistant film the prior art has modified the water resistant polymer. One of the more useful ways of modifying polymers involves blending them with other polymers of different structures and properties.

Polymer blends of polyolefins and poly(ethylene oxide) have been shown to be water modifiable at expectedly low weight % polyolefin levels. Such blends would be anticipated to be flushable when exposed to water in a toilet but do not possess the dry mechanical properties required for functionality in use. Moreover, the high content of poly(ethylene oxide) makes such materials prohibitively expensive for use in a disposable personal hygiene article such as a sanitary napkin, diaper and the like. Polymer blends of polyolefins and poly(ethylene oxide) containing greater than about 45 weight percent of polyolefin are generally water resistant and are not water modifiable. In view of the problems of the prior art, it remains highly desirable to provide a water modifiable film having a substantial portion of thereof composed of a polyolefin. More desirably, the water modifiable film should have greater than about 55 weight percent of a polyolefin. When dry, the film should have the mechanical properties necessary for functionality. When wet, the film should lose at least a portion of its mechanical properties which would render the film flushable and transportable in a sewer system. Such films could be used for making flushable barrier films for personal care products.

It is therefore an object of the invention to provide a polyolefin-containing film that is water modifiable or water-degradable which contains higher levels of polyolefin content. More specifically, it is an object of the invention to provide a polyolefin-containing film having greater than about 55 weight percent of a polyolefin and less than about 45 weight percent of poly(ethylene oxide) that is water-modifiable or water degradable.

SUMMARY OF THE INVENTION

In its principal embodiment, the present invention provides a water degradeable polyolefin-containing film comprising greater than about 55 weight percent of a polyolefin and less than about 45 weight percent of poly(ethylene oxide) wherein the poly(ethylene oxide) has a weight average molecular weight of less than about 100,000. The film of the invention has a loss of at least 10% in two or more tensile properties selected from percent strain-to-break, peak stress, energy-to-break and modulus after being immersed in water for 30 seconds.

In an alternative embodiment, the present invention provides a flushable personal care article having a backing or barrier film comprising greater than about 55 weight percent of a polyolefin and less than about 45 weight percent of poly(ethylene oxide) wherein the poly(ethylene oxide) has a molecular weight of less than about 100,000. The film of the invention has a loss of at least 10% in two or more tensile properties selected from percent strain-to-break, peak stress, energy-to-break and modulus after being immersed in water for 30 seconds.

DETAILED DESCRIPTION OF THE INVENTION

As used herein "water modifiable" or "water degradable" means that a four mil thick film (one mil equals 0.001 of an inch or 0.025 mm), when immersed in water for 30 seconds, will have been modified by greater than 10% two or more of the following tensile properties: percent strain-to-break, peak stress, energy-to-break, and modulus. To determine the degree of modification, the "wet" values are compared to the pre-immersed or "dry" film values.

The term "personal care product" or "personal care article" means articles such as infant diapers, sanitary napkins, adult incontinence garments, and the like.

By the term "backing layer" or "barrier layer" is meant that component of an infant diaper, sanitary napkin, adult incontinence garment or the like which is worn during normal use furthest from the user's body and which serves to minimize or prevent the exudation of the absorbed liquid.

Although the present invention is described with reference to a water modifiable film and, in particular, to personal care articles having a backing layer, liner, or barrier layer comprising such films, one skilled in the art will understand that the composition of the invention can be used to make other thermoplastic articles that can be extruded or injection molded in which the desired property of water degradability is needed, such as packaging articles and the like.

In one embodiment of the invention, the water modifiable or water-degradable film comprises greater than about 55 weight percent of a polyolefin and less than about 45 weight percent of poly(ethylene oxide). Desirably, the water-modifiable film comprises from about 55 weight percent to about 85 weight percent of a polyolefin and from about 45 weight percent to about 15 weight percent of poly(ethylene oxide). More desirably, the water modifiable film comprises from about 65 weight percent to about 85 weight percent of a polyolefin and from about 35 weight percent to about 15 weight percent of polylethylene oxide). The poly(ethylene oxide) useful in making the film has a weight average molecular weight of less than about 100,000. The preferred polyolefin is polyethylene, with low density polyethylene ("LDPE") being particularly preferred.

The saturated ethylene polymers useful in the practice of this invention are homopolymers of ethylene, preferably low density polyethylene, and are essentially linear in structure. As used herein, the term "saturated" refers to polymers which are fully saturated, but also includes polymers containing up to about 5% unsaturation.

Low density polyethylene suitable for use in the films of this invention has a density of less than 0.94 g/cc and are usually in the range of 0.91 g/cc to about 0.93 g/cc. Low density polyethylene has a melt index ranging from about 0.05 dg/min to about 100 dg/min and desirably from 0.05 dg/min to about 20 dg/min. Ultra low density polyethylene also can be used in accordance with the present invention. Generally, ultra low density polyethylene has a density of less than 0.90 g/cc.

A suitable commercially available low density polyethylene material for use in the polymer film blends of the present invention is LDPE 501I available from Dow Plastics Division of Dow Chemical Co., Midland, Mich. The resin has a density of 0.922 g/cm$^3$ and a melt index of 1.9 dg/min.

A suitable low molecular weight poly(ethylene oxide) for use in the polymer blends of the present invention is available from Union Carbide Corporation, Danbury, Conn. under the trade name of POLYOX® Grade WSN-10 having a weight average molecular weight of 100,000. Typically, poly(ethylene oxide) is a dry free flowing white powder having a crystalline melting point in the order of about 650C., above which poly(ethylene oxide) resin becomes thermoplastic and can be formed by molding, extrusion and other methods known in the art.

The water-modifiable or water degradable polyolefin-containing films of the present invention, when immersed in water for about 30 seconds, lose greater than 10% in at least two of the tensile properties: percent stain-to-break, peak stress, energy-to break and modulus. Typically, at least two of the tensile properties will be reduced greater than about 25%, more typically, by about 25% to about 98%, and even more typically by at least about 30% to about 80%. The values in determining the extent of loss of the tensile property or properties modification are relative to the dry condition, i.e. pre-immersion value for that measured property.

The present invention is illustrated in greater detail by the specific examples presented below. It is to be understood that these examples are illustrative embodiments and are not intended to be limiting of the invention, but rather are to be construed broadly within the scope and content of the appended claims.

Comparative Example A

A 60/40 weight percent blend of low density polyethylene (PE) having a melt index of 1.9 decigrams per minute (dg/min) and a density of 0.922 grams per cubic centimeter (g/cc) (Dow 503I; available from Dow Chemical Company, Midland, Mich.) and poly(ethylene oxide) (PEO) having a molecular weight of 200,000 g/mol (POLYOX® WSRN-80 available from Union Carbide Corp., Danbury, Conn.) was fed to a Haake counter-rotating twin screw extruder at a rate of 5 lb/hr (2.27 kg/hr). The extruder had a length of 300 millimeters. Each conical screw had 30 millimeters diameter at the feed port and a diameter of 20 millimeters at the die. The extruder had four heating zones set at 170° C., 180° C., 180° C. and 190° C. The screw speed of the extruder was 150 rpm.

Film processing of all the blends was performed using a Haake extruder counter-rotating twin screw extruder as described above with the following modifications. The extruder included a 4 inch (101.6 mm) slit die at a temperature of 195° C. The screw speed was at 30 rpm. A chilled wind-up roll was used to collect the film. The chilled roll was operated at a speed sufficient to form a film having a thickness of about 4 mils (about 0.102 mm) and was maintained at a temperature of 15–20° C. Dry tensile tests were performed on a Sintech 1/D tensile tester available from MTS Systems Corp., Machesny Park, Ill. The film was cut into a type V dogbone shape in accordance with ASTM D638. The test was performed with a grip separation of 30 millimeters and a crosshead speed of 4 millimeters/second.

Wet tensile tests were performed on a Vitrodyne V1000 mini-tensile tester available from Chatillon, Greensboro, N.C. The film samples were placed in the grips and the testing apparatus was submerged in ambient temperature, non-stirred water for 30 seconds. The test was then run under the same conditions as the dry tensile test. Peak stress, percent strain-to-break, energy-to-break (as area under stress versus strain curve) and modulus were calculated using the actual stress versus strain values recorded from the tensile tester for each dry or wet tensile test. The peak stress was recorded as the greatest stress value. The percent stain-to-break was recorded as the percent strain value at break. The energy-to-break (area under stress versus stain curve) was calculated by the summation of rectangular "slices" under the curve determined for each strain value recorded from the tensile test, using the following formula:

$$((\text{Strain value}_x - \text{Strain value}_{x-1}) \times (\text{Stress value}_x + \text{Stress value}_{x-1}))/2$$

where "X" is the sequential number of the slice. The modulus was calculated by linear regression of the initial region of the stress versus strain curve. The dry and wet properties of the film produced from the blend in Comparative Example A are indicated in Table 1 below.

TABLE 1

Percent Loss in Tensile Properties
Comparative Example A

| Property | Dry | Wet | Percent Loss from Dry to Wet |
|---|---|---|---|
| Thickness (mil) | 4.1 | 4.2 | |
| Percent Strain | 550 | 500 | 9 |
| Peak Stress (MPa) | 16.6 | 16.2 | 2 |
| Energy-to-Break (× 10⁶ J/m³) | 65.7 | 64.0 | 3 |
| Modulus | 77.0 | 62.3 | 19 |

This example shows that a polymer blend of low density polyethylene with poly(ethylene oxide) having a weight average molecular weight of 200,000 is water resistant. The polymer blend was not water modifiable after 30 seconds of immersion in water.

EXAMPLE 1

In Example 1, a Werner & Pfleiderer ZSK-30 extruder (available from Werner & Pfleiderer, Ramsey, N.J.) was used. The extruder had a pair of co-rotating screws arranged in parallel. The center distance between the two shafts was 26.2 mm. The nominal screw diameter was 30 mm. The actual outer screw diameter was 30 mm. The inner screw diameter was 21.3 mm. The thread depth was 4.7 mm. The extruder had 14 processing barrels, with 13 heated barrels divided into 7 heating zones. The overall processing length was 1340 mm.

A 60/40 weight percent resin blend of low density polyethylene (Dow 503I) and poly(ethylene oxide) having a weight average molecular weight of about 100,000 g/mol (Union Carbide POLYOX® WSRN-10) was fed to the ZSK-30 extruder at a rate of 35 lb/hr (15.91 kg/hr). The seven heating zones were all set at 180° C. The screw speed was 300 rpm.

The dry and wet properties of the film produced from the blend in Example 1 are indicated in Table 2 below.

TABLE 2

Percent Loss in Tensile Properties
Example 1

| Property | Dry | Wet | Percent Loss from Dry to Wet |
|---|---|---|---|
| Thickness (mil) | 3.2 | 3.2 | |
| Percent Strain | 717 | 100 | 96 |
| Peak Stress (MPa) | 11.3 | 3.6 | 68 |
| Energy-to-Break (× 10⁶ J/m³) | 65.8 | 2.7 | 96 |
| Modulus (Mpa) | 96.0 | 27.2 | 72 |

In accordance with the invention, Example 1 was a film of a polymer blend of 60 weight percent of an unmodified polyethylene and 40 weight percent an unmodified poly (ethylene oxide) having a weight average molecular weight of about 100,000. The film of this polymer blend was water degraded after 30 seconds of submersion in water as shown by the data showing percent loss tensile properties of greater than 68% from dry to wet in all properties tested and greater than 86% loss in percent strain and energy-to-break.

While the invention has been described with reference to the preferred embodiments and illustrated with regard to a range of optional features, those skilled in the art will appreciate that various substitutions, omissions, changes and modifications may be made without departing from the spirit of the invention as it is defined by the appended claims. Accordingly, it is intended that the foregoing description be deemed merely exemplary of the preferred scope of the present invention and not be deemed a limitation thereof.

We claim:

1. A water-degradable personal care article having a backing or barrier layer comprising a polyolefin-containing film comprising from about 55 to 85 weight percent of a polyolefin and from about 15 to 45 weight percent of unmodified poly(ethylene oxide), wherein said unmodified poly(ethylene oxide) has a weight average molecular weight of less than about 100,000, said film having a loss of at least 60% in at least two tensile properties selected from percent strain-to-break, peak stress, energy-to-break and modulus after being immersed in water for 30 seconds.

2. A personal care article according to claim 1 wherein said backing or barrier layer comprises about 60 weight percent of a polyolefin and about 40 weight percent unmodified poly(ethylene oxide).

3. A personal care article according to claim 1 wherein said article is a feminine hygiene napkin.

4. A personal care article according to claim 1 wherein said article is an infant diaper.

5. A personal care article according to claim 1 wherein said article is an adult incontinence garment.

6. A personal care article according to claim 1 wherein said polyolefin is polyethylene.

7. A personal care article according to claim 2 wherein said polyolefin is polyethylene.

8. A personal care article according to claim 6 wherein said polyethylene is low density polyethlene.

9. A personal care article according to claim 7 wherein said polyethylene is low density polyethylene.

* * * * *

UNITED STATES PATENT AND TRADEMARK OFFICE
CERTIFICATE OF CORRECTION

PATENT NO. : 6,153,700  
DATED : November 28, 2000  
INVENTOR(S) : James H. Wang et al.

Page 1 of 1

It is certified that error appears in the above-identified patent and that said Letters Patent is hereby corrected as shown below:

Title page,
Item [54], delete "WATER-DEGRADABLE FLUSHABLE FILM OF POLYOLEFIN AND POLY(ETHYLENE OXIDE) AND PERSONAL CARE ARTICLE THEREWITH" and insert -- WATER-MODIFIABLE FLUSHABLE POLYOLEFIN-CONTAINING FILM AND ARTICLE MADE THEREFROM -- in place thereof.

Column 6, TABLE 2,
Line 9, for "Percent Strain" under "Percent Loss from Dry to Wet", delete "96" and insert -- 86 -- in place thereof.

Signed and Sealed this

First Day of January, 2002

Attest:

Attesting Officer

JAMES E. ROGAN  
*Director of the United States Patent and Trademark Office*